United States Patent
Perschbacher et al.

(10) Patent No.: US 7,277,750 B2
(45) Date of Patent: Oct. 2, 2007

(54) METHOD AND APPARATUS FOR ANTI-TACHYCARDIA PACING AND DEFIBRILLATION

(75) Inventors: David L. Perschbacher, Coon Rapids, MN (US); Karin K. Roof, St. Paul, MN (US); Rebecca Bloomfield, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 376 days.

(21) Appl. No.: 10/817,751

(22) Filed: Apr. 2, 2004

(65) Prior Publication Data

US 2005/0222629 A1   Oct. 6, 2005

(51) Int. Cl.
*A61N 1/362* (2006.01)
*A61N 1/39* (2006.01)

(52) U.S. Cl. ............... 607/4; 607/5; 607/7; 607/12; 607/14

(58) Field of Classification Search .......... 607/4–5, 607/7, 12, 14
See application file for complete search history.

(56) References Cited

U.S. PATENT DOCUMENTS

| | | | |
|---|---|---|---|
| 5,163,429 A | 11/1992 | Cohen | |
| 5,318,591 A | 6/1994 | Causey, III et al. | |
| 5,458,619 A | 10/1995 | Olson | |
| 5,607,385 A | 3/1997 | Fransischelli et al. | |
| 5,713,924 A | 2/1998 | Min et al. | |
| 5,814,079 A | 9/1998 | Kieval | |
| 5,913,878 A * | 6/1999 | Hsung et al. | 607/5 |
| 5,978,707 A | 11/1999 | Krig et al. | |
| 6,151,524 A | 11/2000 | Krig et al. | |
| 6,230,055 B1 | 5/2001 | Sun et al. | |
| 6,317,632 B1 | 11/2001 | Krig et al. | |
| 6,330,477 B1 | 12/2001 | Casavant | |
| 6,400,986 B1 | 6/2002 | Sun et al. | |
| 6,415,175 B1 | 7/2002 | Conley et al. | |
| 6,418,340 B1 | 7/2002 | Conley et al. | |
| 6,442,426 B1 | 8/2002 | Kroll | |
| 2002/0147407 A1 | 10/2002 | Seim | |
| 2003/0023273 A1 | 1/2003 | DeGroot et al. | |
| 2003/0088291 A1 | 5/2003 | Anderson et al. | |
| 2003/0199927 A1 * | 10/2003 | Ousdigian et al. | 607/4 |
| 2003/0204210 A1 | 10/2003 | Ousdigian et al. | |

OTHER PUBLICATIONS

"International Search Report and Written Opinion for Application No. PCT/US2005/011769, date mailed Aug. 24, 2005", 14 Pages.

* cited by examiner

*Primary Examiner*—Carl Layno
*Assistant Examiner*—Shevon E Johnson
(74) *Attorney, Agent, or Firm*—Schwegman, Lundberg, & Woessner, P.A.

(57) ABSTRACT

An implantable cardioverter/defibrillator (ICD) includes an Anti-Tachycardia Pacing Before Charge (ATP-BC) mode according to which one or more high-voltage capacitors for storing defibrillation energy are charged in preparation of delivering a defibrillation shock only if a ventricular tachycardia (VT) sustains after an ATP delivery. Fast ATP delivery and effect verification methods are applied to avoid significant delay in delivering the defibrillation shock when found necessary to terminate the VT. A switch is provided such that a user decides whether to activate the ATP-BC mode or to deliver the defibrillation shock without delivering the ATP.

45 Claims, 6 Drawing Sheets

Fig.5

US 7,277,750 B2

METHOD AND APPARATUS FOR ANTI-TACHYCARDIA PACING AND DEFIBRILLATION

FIELD OF THE INVENTION

This document generally relates to cardiac rhythm management systems and particularly, but not by way of limitation, to such systems providing for anti-tachycardia pacing (ATP) and defibrillation.

BACKGROUND

Tachyarrhythmias are abnormal heart rhythms characterized by a rapid heart rate. Tachyarrhythmias generally include supraventricular tachycardia (SVT, including atrial tachycardia, AT) and ventricular tachycardia (VT). Fibrillation is a form of tachycardia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. VT occurs when the electrical impulses re-enter the atria from the ventricles to form a self-sustaining conductive loop or when a natural pacemaker in a ventricle usurps control of the heart rate from the sinoatrial node. When the heart rate reaches certain levels, the ventricles contracts before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory.

Another type of electrical therapy for tachycardia is anti-tachycardia pacing (ATP). In ATP, the heart is competitively paced in an effort to interrupt the reentrant circuit causing the tachycardia. An exemplary ICD's includes ATP and defibrillation capabilities so that ATP is delivered to the heart when VT is detected, while a defibrillation shock is delivered when fibrillation occurs. Although cardioversion and/or defibrillation are effective in terminating tachycardia, it consumes a large amount of power and results in patient discomfort owing to the high voltage of the shock pulses. It is desirable, therefore, for the ICD to use ATP to terminate a tachyarrhythmia whenever possible.

In one practice, a VT with a heart rate that is not extremely high (e.g., 180 beats per minute or less) is treated with ATP therapy in order to avoid an unnecessary painful shock to the patient, and a defibrillation shock is delivered if the pacing fails to terminate the tachyarrhythmia. However, when the heart rate is considered extremely high, many physicians are reluctant to apply ATP and choose to defibrillate immediately, even though studies have showed that ATP is still effective for a substantial majority of the patients. The primary concern is that an unsuccessful ATP therapy delays the delivery of defibrillation therapy, and that delay may comprise the effectiveness of the defibrillation therapy.

For these and other reasons, there is a need for a safe and efficient way to avoid the delivery of unnecessary defibrillation shocks and the waste of energy.

SUMMARY

In one embodiment of a system according to the present subject matter, a CRM system includes a sensing circuit, a pacing circuit, a defibrillation circuit, a VT detector, a VT verification module, and a controller, each as described below. The sensing circuit senses a cardiac signal. The pacing circuit delivers ATP. The defibrillation circuit delivers a shock, and includes a defibrillation capacitor to store an electrical energy for the shock and a capacitor charging circuit to charge the defibrillation capacitor in response to a charging signal. The VT detector detects a VT based on at least the cardiac signal. The VT verification module receives a first VT verification command and a second VT verification command and performs a VT verification test to determine whether the VT sustains based on at least the cardiac signal after one of the first and second VT verification commands is received. The controller includes an ATP activator, a first VT verification controller, an ATP controller, a second VT verification controller, a charging controller, and a defibrillation controller. The ATP activator receives an ATP activation command and, in response, produces an ATP activation signal. The first VT verification controller issues the first VT verification command after the VT is detected and produces a first VT verification signal if the VT sustains after being detected. The ATP controller detects a presence of the ATP activation signal. If the ATP activation signal is present, the ATP controller receives the first VT verification signal and controls an ATP delivery after the first VT verification signal is received. The second VT verification controller issues the second VT verification command after the ATP delivery and produces a second VT verification signal if the VT sustains after the ATP delivery. The charging controller detects the presence of the ATP activation signal. If the ATP activation signal is present, the charging controller receives the second VT verification signal and produces the charging signal after the second VT verification signal is received. If the ATP activation signal is not present, the charging controller receives the first VT verification signal and produces the charging signal after the first VT verification signal is received. The defibrillation controller controls a delivery of the shock after the charging of the defibrillation capacitor is completed.

In one embodiment of a method according to the present subject matter, an ATP activation command is received to activate a mode of ICD operation as described below. The ATP activation command activates a feature including delivering an ATP. A VT is detected, and whether the VT sustains after being detected is determined. If the ATP activation command is received and the VT sustains after being detected, ATP is delivered. Whether the VT sustains after the ATP delivered is determined. If the VT sustains after the ATP is delivered, a defibrillation capacitor is charged, and a defibrillation shock is delivered after the capacitor is charged.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this document are not necessarily to the same embodiment, and such references contemplate more than one embodiment.

In this document, "defibrillation" generally includes cardioversion and defibrillation. A "user" includes a physician or other caregiver treating the patient having the ICD implanted.

This document discusses, among other things, an embodiment of a CRM system including an ICD capable of delivering ATP, verifying the effect of ATP, and delivering defibrillation shocks. The ICD includes an ATP Before Charge (ATP-BC) mode. In response to a VT episode detected while the ATP-BC mode is active, the ICD delivers the ATP and verifies the effect of ATP in terminating the VT. Only if the VT sustains after an ATP delivery, the ICD charges its one or more defibrillation capacitors (high-voltage capacitors for storing the energy to be released as the defibrillation shock).

If the VT is terminated by the ATP, the patient need not receive the defibrillation shock, which causes substantial discomfort. Because the VT may sustain after the ATP delivery, any delay in the defibrillation therapy associated with the ATP delivery must be reasonably short to ensure a timely delivery of the defibrillation shock, if needed. One approach to minimization or elimination of the delay is to deliver the ATP while charging the defibrillation capacitors. If the VT is terminated by the ATP, the shock is avoided, but the energy charged into the defibrillation capacitors is lost. One further approach is to establish a certain level of confidence by delivering the ATP while charging the defibrillation capacitors, and switching to the ATP-BC mode only if the ATP has successfully terminated the VT for a certain number of attempts. This approach still results in substantial loss of energy, thereby shortening the longevity of the ICD.

In accordance with the present subject matter, safety of operating the ICD in the ATP-BC mode is ensured by (i) using fast ATP delivery and effective verification methods to avoid a significant delay in delivering the defibrillation shock, and (ii) providing the user with means for activating the ATP-BC mode. If the ATP-BC mode is not activated, the ICD delivers the defibrillation shock without delivering the ATP, at least when the detected VT falls into a ventricular fibrillation (VF) detection window (e.g., with a heart rate between 180 and 250 beats per minute (bpm)). Because a patient's cardiovascular and other conditions progress over time, it is advantageous to allow the user to decide whether to activate the ATP-BC mode based on the patient's individual, up-to-date conditions and circumstances. Such conditions and circumstances may not be completely analyzable by the ICD or the system coupled to the ICD. Thus, in one embodiment, the present subject matter allows the user to apply his or her medical evaluation and judgment in the process of deciding whether the ATP-BC is suitable for each individual patient, instead of depending on the ICD or other device to make the decision.

Figure 1:
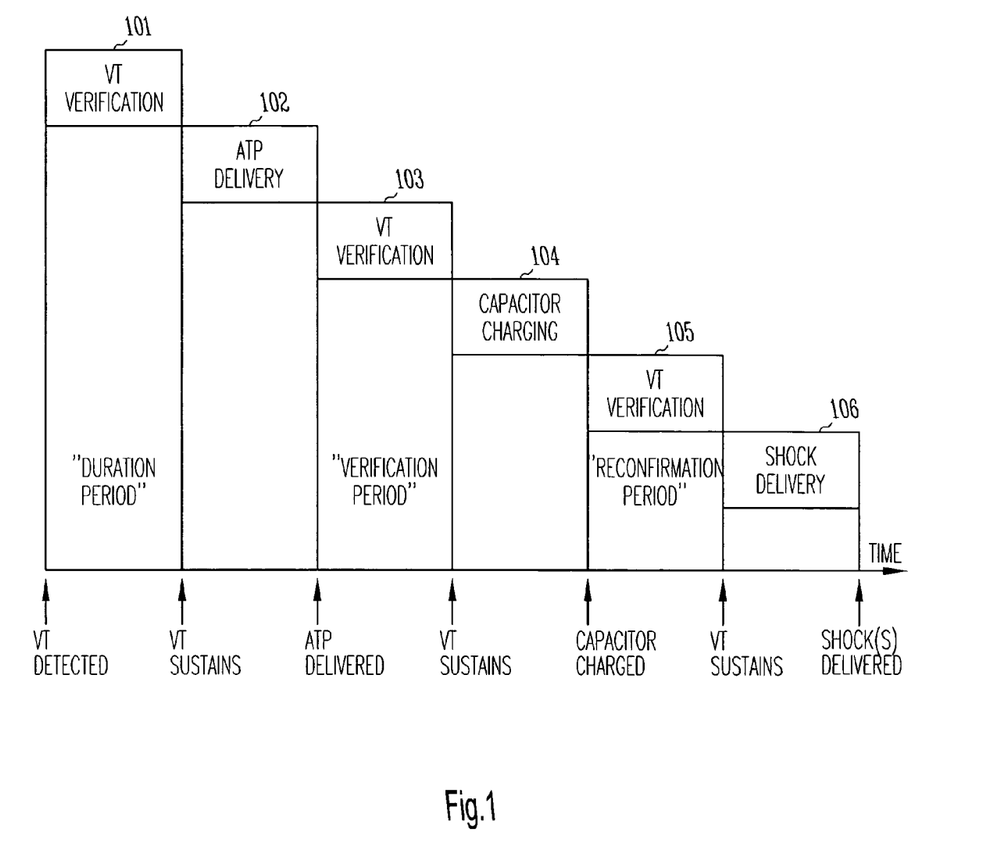
FIG. 1 is a timing diagram illustrating an embodiment of a method for operating an ICD in an ATP-BC mode.

FIG. 1 is a timing diagram illustrating an embodiment of a method for operating the ICD in the ATP-BC mode. The ATP-BC mode starts when a VT episode is detected and includes a VT verification interval 101, an ATP delivery interval 102, another VT verification interval 103, a capacitor charging interval 104, another VT verification interval 105, and a shock delivery interval 106. Generally, each of intervals 102-106 starts after the previously interval ends.

VT verification interval 101, also referred to as the "duration period," starts with a detection of the VT episode. The purpose is to confirm that the detected VT sustains and therefore requires a therapy. In one embodiment, the VT is considered sustained if the VT remains present at the end of VT verification interval 101. A fast VT verification test is performed during VT verification interval 101. In one embodiment, the fast VT verification test declares that the VT sustains if at least M out of N consecutive heart beats are detected as fast beats, where M and N are predetermined numbers, and fast beats are heart beats each characterized with a heart rate within a programmable VT detection window. In one specific embodiment, the fast VT verification test declares that the VT sustains if at least 6 out of 10 consecutive heart beats are detected as fast beats. In one specific embodiment, the fast VT verification test declares that the VT sustains if at least 8 out of 10 consecutive heart beats are detected as fast beats. In one specific embodiment, after 3 (or another predetermined number) consecutive fast beats are detected, the fast VT verification test detects heart rates for 10 consecutive beats including the 3 consecutive beats, and declares that the VT sustains if at least 6 (or 8) out of the 10 consecutive heart beats are detected as fast beats.

In one embodiment, the VT detection window includes a VF detection window. In one embodiment, the VT detection window is defined by one or more threshold rates. In one specific embodiment, the VT detection window includes an upper threshold rate of 250 bpm. That is, VT treatment using ATP is attempted only if the heart rate is below 250 bpm. If the heart rate is 250 bpm or above, ATP delivery interval 102 and VT verification interval 103 are skipped. In one specific embodiment, the VT detection window is defined by a threshold rate window of about 180-250 bpm. That is, VT treatment using ATP is attempted only if the heart rate is between about 180 bpm and 250 bpm. If the heart rate is outside the 180-250 bpm window, ATP delivery interval 102 and VT verification interval 103 are skipped. If the average heart rate for the 10 consecutive heart beats is about 200 bpm, the fast VT verification test, and hence VT verification interval 101, lasts about 3 seconds. In one embodiment, VT verification interval 101 includes a precharging period during which the ICD charges its defibrillation capacitor(s).

ATP delivery interval 102 starts after VT verification interval 101 if the VT sustains. In one embodiment, ATP delivery interval 102 starts after VT verification interval 101 if the VT sustains and if the heart rate does not exceed a programmable limit. In a specific embodiment, ATP delivery interval 102 starts only if the average heart rate or ventricular rate is below 250 bpm. The ATP includes delivery of a burst of pacing pulses. In one specific embodiment, the burst includes 8 pacing pulses with a pacing interval being a preset or programmable percentage of the coupling interval, which is a programmable time interval between the last detected intrinsic depolarization and the first pacing pulse of the first burst. In one embodiment, the coupled interval is programmable within a range of 120 ms to 750 ms. In one embodiment, the pacing interval (burst cycle length) is set to be 88% of the coupling interval or 200 ms, whichever is longer. If the average heart rate for the 10 consecutive heart beats is about 200 bpm, the delivery of the first burst takes about 2 seconds.

VT verification interval 103, also referred to as the "verification period," starts upon the end of ATP delivery interval 102. The purpose is to determine whether a further therapy, i.e., defibrillation, is required by determining whether the VT sustains after the ATP delivery. In one embodiment, the VT is considered sustained if the VT is detected at the end of VT verification interval 103. In one embodiment, the fast VT verification test performed during VT verification interval 101 is repeated during VT verification interval 103.

In one embodiment, only one burst of 8 pacing pulses is delivered in the attempt to terminate the VT by ATP. In another embodiment, one or more additional bursts of pacing pulses are delivered, and ATP delivery internal 102 and VT verification interval 103 are repeated for each additional burst delivered. The repetition stops either after a fast VT verification test declares that the VT is no longer present or after a predetermined maximum number of repetitions has been reached. Each additional burst includes 8 pacing pulses with a pacing interval (burst cycle length) set to be 88% of the burst cycle length or 200 ms, whichever is longer. If the average heart rate for the 10 consecutive heart beats remains at about 200 bpm, the delivery of each additional burst takes about 2 seconds.

Capacitor charging interval 104 starts upon the end of VT verification interval 103 if the VT sustains after the ATP delivery. During capacitor charging interval 104, the defibrillation capacitor(s) are charged to the level required for delivering the defibrillation shock. If the fast verification test is performed each time over 10 consecutive heart beats having an average heart rate of 200 bpm, and one burst of 8 pacing pulses is delivered in the attempt to terminate the VT by ATP, the overall time interval from the detection of the VT to the beginning of capacitor charging (i.e., the sum of intervals 101, 102, and 103) is about 8 to 9 seconds (including "skipped" beats, or transitional heart beats not included as part of the ATP nor the fast verification tests). In one embodiment, another VT verification is performed while the defibrillation capacitor(s) are being charged to determine whether the capacitor charging should continue and whether the defibrillation shock is required. In one specific embodiment, the fast VT verification test performed during VT verification interval 101 is repeated during capacitor charging interval 104. If VT ceases to be present during capacitor charging interval 104, the capacitor charging stops and no defibrillation shock is delivered.

VT verification interval 105, also referred to as the "reconfirmation period," starts near or upon the end of capacitor charging interval 104. The purpose is to perform a final confirmation on whether the defibrillation shock is required by determining whether the VT sustains after the defibrillation capacitor(s) are charged. In one embodiment, the VT is considered sustained if the VT is detected at the end of VT verification interval 105. In one embodiment, the fast VT verification test performed during VT verification interval 101 is repeated during VT verification interval 105. In one embodiment, VT verification interval 105 applies only if the ICD is programmed to include the final confirmation.

Shock delivery interval 106 starts upon the end of VT verification interval 105 if the VT sustains after the defibrillation capacitors are charged. A defibrillation shock is delivered to the heart to terminate the VT. In one embodiment, the fast VT verification test performed during VT verification interval 101 is repeated after the shock delivery. In one specific embodiment, the fast VT verification test performed after the shock therapy declares that the VT sustains if at least 8 out of 10 consecutive heart beats are detected as fast beats. If the VT sustains, the defibrillation capacitors are charged and the defibrillation shock is delivered again. This verification-charging-shock delivery step is repeated during shock delivery interval 106 until the fast VT verification test declares that the VT no longer sustains.

Figure 2:
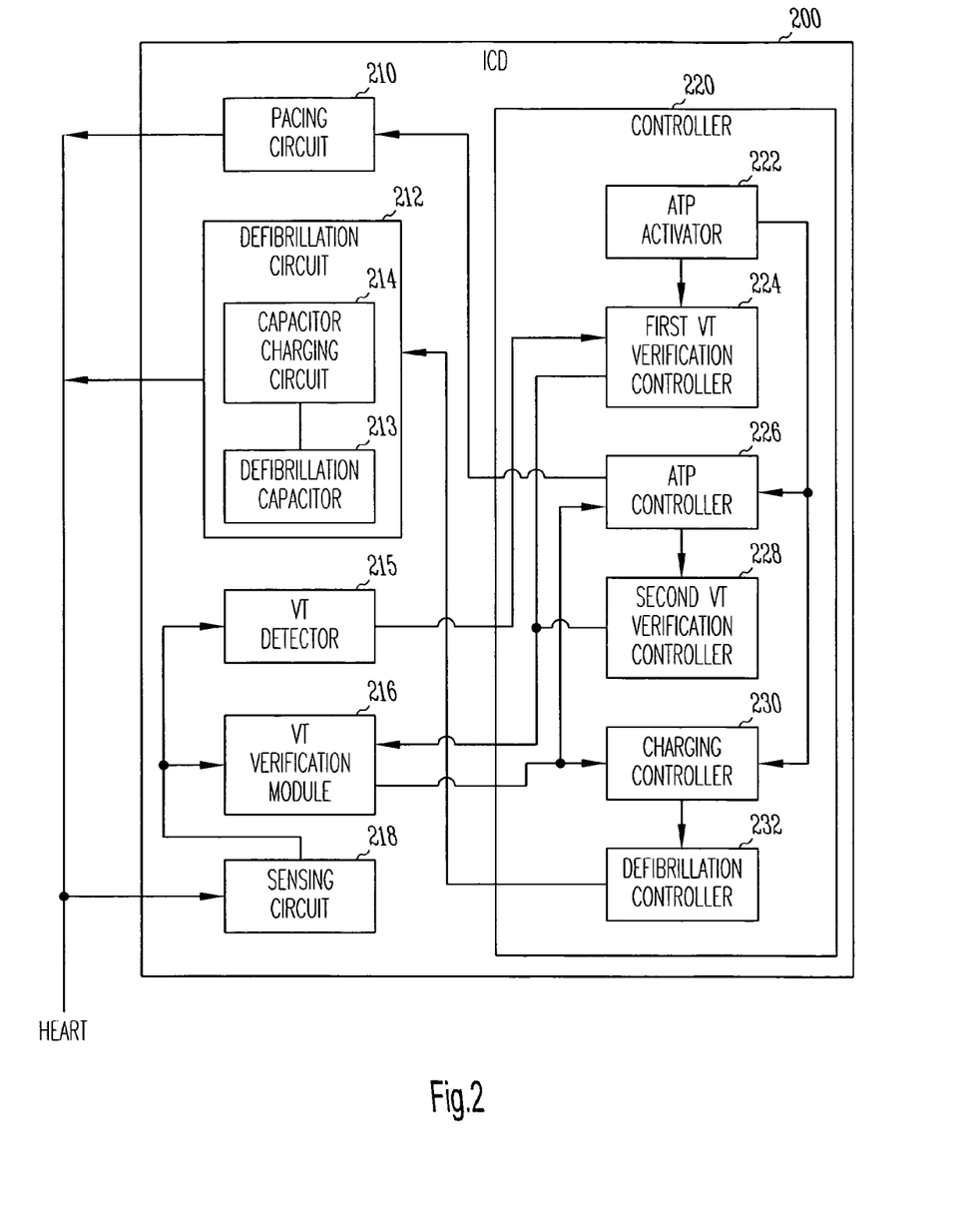
FIG. 2 is block diagram showing one embodiment of portions of the circuit of the ICD performing the method of FIG. 1.

FIG. 2 is block diagram showing one embodiment of portions of the circuit of an ICD 200 capable of performing the method of the ATP-BC as discussed above. ICD 200 includes a pacing circuit 210, a defibrillation circuit 212, a VT detector 215, a VT verification module 216, a sensing circuit 218, and a controller 220. A hermetically sealed, biocompatible metal can houses all or substantially all of these ICD device elements. After being implanted into a patient, ICD 200 connects to the patient's heart through a lead system including pacing and defibrillation leads.

Pacing circuit 210 delivers the ATP to the heart. In one embodiment, pacing circuit 210 also delivers pacing pulses according to one or more other pacing algorithms for such as bradycardia pacing, cardiac resynchronization therapy, or remodeling control therapy. Pacing circuit 210 delivers pacing pulses to the heart through one or more leads each having at least one electrode placed in or on the heart.

Defibrillation circuit 212 delivers defibrillation shocks to the heart through one or more leads each having at least one electrode placed in or on the heart. Defibrillation circuit 212 includes a defibrillation capacitor 213 and a capacitor charging circuit 214 to charge capacitors 213. Defibrillation capacitor 213 includes one or more capacitors, as part of ICD 200, for storing the energy for each delivery of the defibrillation shocks. Capacitor charging circuit 214 charges defibrillation capacitor 213 when a delivery of the defibrillation shock is commanded. Defibrillation circuit 212 delivers the defibrillation shock after the capacitor charging is completed.

Sensing circuit 218 senses one or more cardiac signals including at least one cardiac signal indicative of the VT episode. In one embodiment, the cardiac signal indicative of the VT episode includes an electrogram acquired through a lead having at least one electrode placed in or on the heart.

Figure 3A:
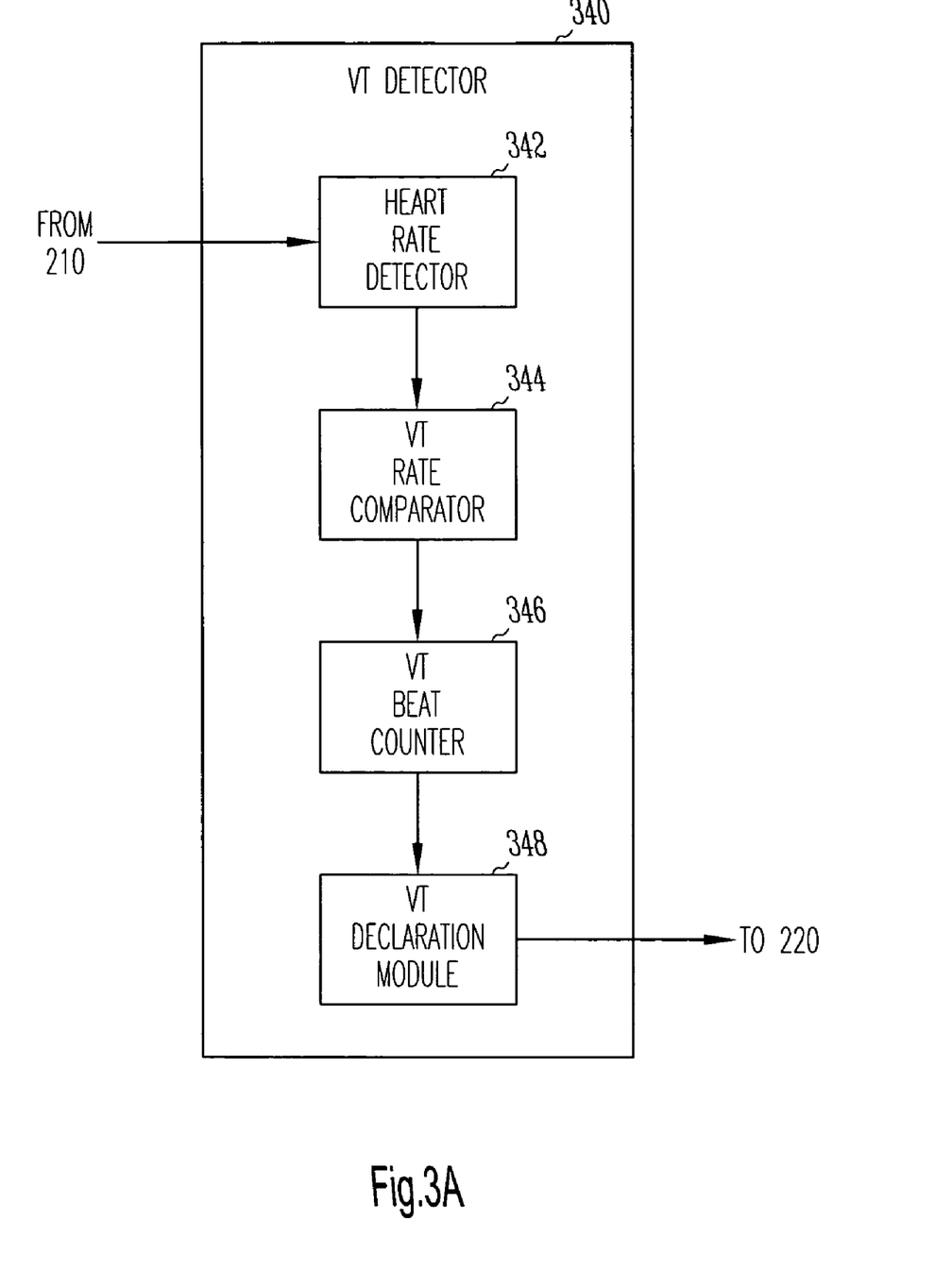
FIG. 3A is block diagram showing one embodiment of portions of the circuit of a VT detector of the ICD.

VT detector 215 is further illustrated in FIG. 3A, a block diagram showing one embodiment of portions of its circuit. VT detector 215 detects the VT from the cardiac signal indicative of the VT episode. In one embodiment, VT detector 215 includes a heart rate detector 342, a VT rate comparator 344, a VT beat counter 346, and a VT declaration module 348. Heart rate detector 342 detects a heart rate for each heart beat of a predetermined number of consecutive heart beats. In one embodiment, VT rate comparator 344 compares the heart rate for each beat to a predetermined VT threshold rate. VT beat counter 346 counts a number of fast beats each being a heart beat having a heart rate exceeding the predetermined VT threshold rate. In another embodiment, VT rate comparator 344 compares the heart rate for each beat to two predetermined VT threshold rates that form a detection window. VT beat counter 346 counts a number of fast beats each being a heart beat having a heart rate falling within the detection window. VT declaration module 348 declares that the VT is detected based on the number of the fast beats and the predetermined number of consecutive heart beats. In one embodiment, VT declaration module 348 includes a VT detection comparator to compare the number of fast beats to a predetermined threshold number and declare that the VT is detected if the number of fast beats exceeds the predetermined threshold number. In one specific embodiment, VT declaration module 348 declares that the VT is detected if at least 8 out of 10 consecutively detected heart beats are fast beats. In another specific embodiment, after 3 consecutive fast beats are detected, heart rate is detected for 10 consecutive beats including the 3 consecutive fast beats, and VT declaration module 348 declares that the VT sustains if at least 8 out of the 10 consecutive heart beats are detected as fast beats. In another embodiment, VT declaration module 348 includes a VT beat ratio calculator to calculate a VT beat ratio of the number of fast beats to the predetermined number of consecutive heart beats, and a VT detection comparator to compare the VT beat ratio to a predetermined threshold ratio and declare that the VT is detected if the VT beat ratio exceeds the predetermined threshold ratio. In one specific embodiment, VT declaration module 348 declares that the VT is detected if at least four fifths of the consecutively detected heart beats are fast beats. In one embodiment, one or more of the predetermined thresholds are programmed through an external programmer. In another embodiment, VT detector 215 includes heart rate detector 342 to detect a heart rate and VT rate comparator 344 to compare the heart rate to one or more predetermined VT threshold rates. In one embodiment, the one or more predetermined VT threshold rates are programmed through an external programmer.

Figure 3B:
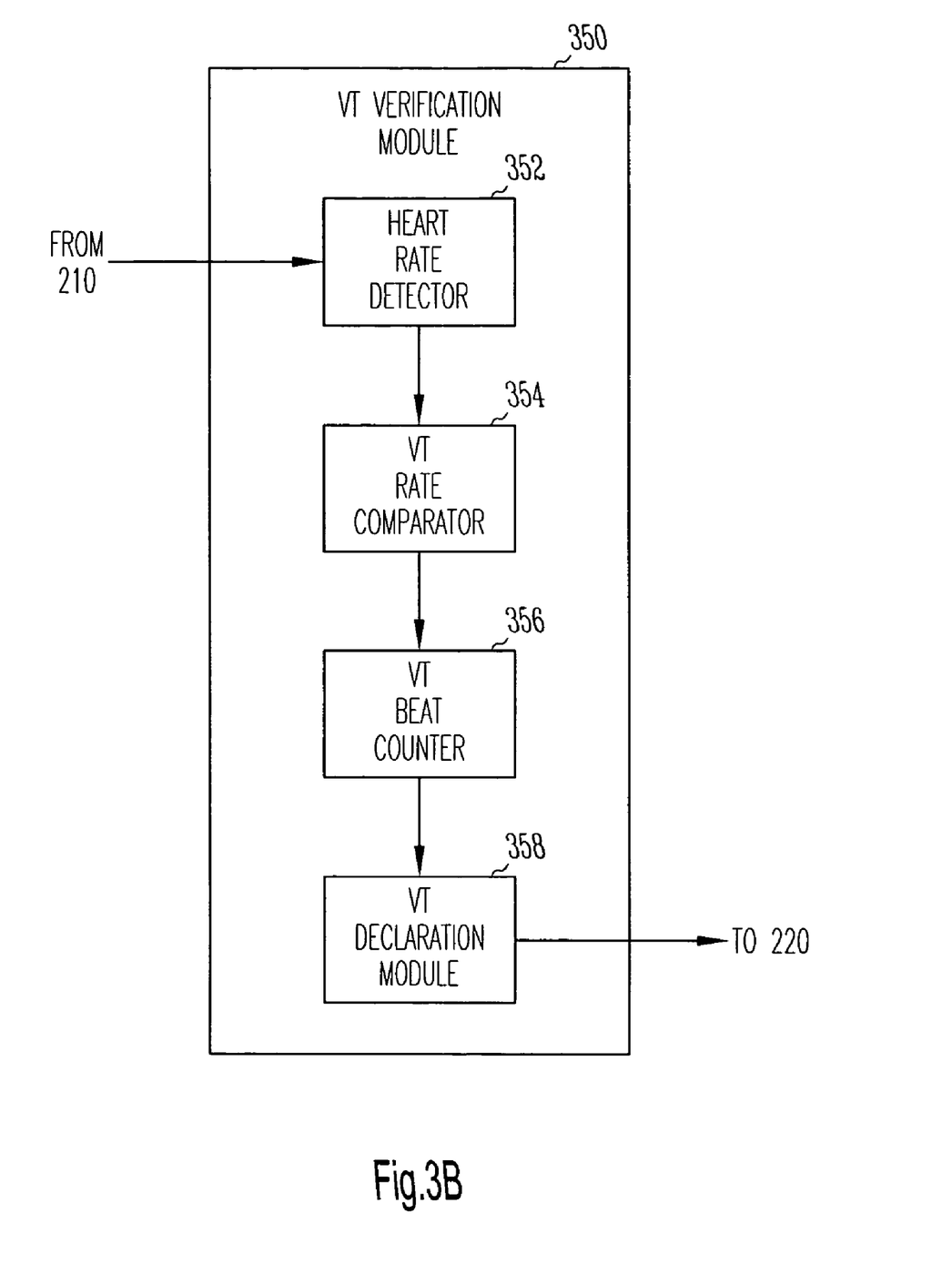
FIG. 3B is block diagram showing one embodiment of portions of the circuit of a VT verification module of the ICD.

VT verification module 216 is further illustrated in FIG. 3B, a block diagram showing one embodiment of portions of its circuit. VT verification module 216 performs the fast VT verification test upon receiving a VT verification command. In one embodiment, VT verification module 216 (i) receives a first VT verification command from controller 220 when a VT episode is detected and performs the fast VT verification test during VT verification interval 101, (ii) receives a second VT verification command from controller 220 after the ATP is delivered and performs the fast VT verification test during VT verification interval 103, (ii) receives a third VT verification command from controller 220 when defibrillation capacitor 213 is being charged and performs the fast VT verification test during capacitor charging interval 104, and (iv) receives a fourth VT verification command from controller 220 after defibrillation capacitor 213 is charged and performs the fast VT verification test during VT verification interval 105. In one embodiment, VT verification module 216 includes a heart rate detector 352, a VT rate comparator 354, a VT beat counter 356, and a VT declaration module 358. Heart rate detector 352 detects a heart rate for each heart beat of a predetermined number of consecutive heart beats. In one embodiment, VT rate comparator 354 compares the heart rate for each beat to a predetermined VT threshold rate. VT beat counter 356 counts a number of fast beats each being a heart beat having a heart rate exceeding the predetermined VT threshold rate. In another embodiment, VT rate comparator 354 compares the heart rate for each beat to two predetermined VT threshold rates forming the detection window. VT beat counter 356 counts a number of fast beats each being a heart beat having a heart rate falling within the detection window. VT declaration module 358 declares that the VT sustains based on the number of the fast beats and the predetermined number of consecutive heart beats. In other words, VT declaration module 358 declares that the VT sustains if the ratio of the number of fast beats to the number of total heart beats exceeds a predetermined threshold. In one embodiment, VT declaration module 358 includes a VT detection comparator to compare the number of fast beats to a predetermined threshold number and declare that the VT sustains if the number of fast beats exceeds the predetermined threshold number. In one specific embodiment, VT declaration module 358 declares that the VT sustains if at least 6 out of 10 consecutively detected heart beats are fast beats. In another specific embodiment, after 3 consecutive fast beats are detected, heart rate is detected for 10 consecutive beats including the 3 consecutive fast beats, and VT declaration module 358 declares that the VT sustains if at least 6 out of the 10 consecutive heart beats are detected as fast beats. In one embodiment, VT declaration module 358 includes a VT beat ratio calculator to calculate a VT beat ratio of the number of fast beats to the predetermined number of consecutive heart beats, and a VT detection comparator to compare the VT beat ratio to a predetermined threshold ratio and declare that the VT sustains if the VT beat ratio exceeds the predetermined threshold ratio. In one specific embodiment, VT declaration module 358 declares that the VT sustains if at least two third of the consecutively detected heart beats are fast beats. In one embodiment, the one or more predetermined VT threshold rates are programmed through an external programmer.

Controller 220, illustrated in FIG. 2, controls the operation of ICD 200 in the ATP-BC mode. In one embodiment, controller 220 starts to control the operation of the ICD in the ATP-BC mode after receiving an ATP activation command from an external programmer. The ATP activation command is an on/off command which determines whether ATP remains as a VT treatment option. If the ATP activation command (an "on"-command) has not been issued, or an ATP deactivation command (an "off"-command) has been issued, defibrillation therapy will be delivered without any attempt to stop VT with ATP. In this embodiment, the user determines whether to operate the ICD in the ATP-BC mode based on the patient's cardiovascular conditions and other circumstances.

Controller 220 includes an ATP activator 222, a first VT verification controller 224, an ATP controller 226, a second VT verification controller 228, a charging controller 230, and a defibrillation controller 232. ATP activator 222 receives the ATP activation command from the external programmer. In response to the ATP activation command, ATP activator 222 produces an ATP activation signal to start the operation in ATP-BC mode. In one embodiment, ATP activator 222 includes a command input to receive the ATP activation command and a heart rate input to receive the heart rate from, for example, heart rate detector 342 or 352. It produces the ATP activation signal in response to the ATP activation command only if the heart rate is below a predetermined threshold rate. In one specific embodiment, the predetermined threshold rate is about 250 bpm. First VT verification controller 224 issues the first VT verification command after the VT is detected for VT verification module 216 to perform the fast VT verification test. If VT verification module 216 declares that the VT sustains after being detected, first VT verification controller 224 produces a first VT verification signal. ATP controller 226 detects the presence of the ATP activation signal. If the ATP activation signal is present, ATP controller 226 receives the first VT verification signal and controls an ATP delivery after the first VT verification signal is received. After the ATP delivery, second VT verification controller 228 issues the second VT verification command for VT verification module 216 to perform the fast VT verification test. If VT verification module 216 declares that the VT sustains after the ATP delivery, second VT verification controller 228 produces a second VT verification signal. Charging controller 230 detects the presence of the ATP activation signal. If the ATP activation signal is present, charging controller 230 receives the second VT verification signal and produces a charging signal for capacitor charging circuit 214 to start charging defibrillation capacitor 213 after the second VT verification signal is received. If the ATP activation signal is not present, charging controller 230 receives the first VT verification signal and produces the charging signal for capacitor charging circuit 214 to start charging defibrillation capacitor 213 after the first VT verification signal is received. Defibrillation controller 232 controls a defibrillation shock delivery after the charge of defibrillation capacitor 213 is completed. In one embodiment, controller 220 further comprises a third VT verification controller. The third VT verification controller issues the third VT verification command when defibrillation capacitor 213 is being charged for VT verification module 216 to perform the fast VT verification test. If VT verification module 216 declares that the VT sustains while defibrillation capacitor 213 is being charged, the third VT verification controller produces a third VT verification signal. Charging controller 230 receives the third VT verification signal and produces a charging termination signal for capacitor charging circuit 214 to stop charging defibrillation capacitor 213. In one embodiment, controller 220 further comprises a fourth VT verification controller. The fourth VT verification controller issues the fourth VT verification command after defibrillation capacitor 213 is charged for VT verification module 216 to perform the fast VT verification test. If VT verification module 216 declares that the VT sustains after defibrillation capacitor 213 is charged, the fourth VT verification controller produces a fourth VT verification signal. Defibrillation controller 232 receives the fourth VT verification signal and controls the delivery of the shock after the third VT verification signal is received. In one embodiment, controller 220 further includes a precharging controller to produce a precharging signal for capacitor charging circuit 214 to charge defibrillation capacitor 213 after the VT is detected and before the ATP delivery.

Figure 4:
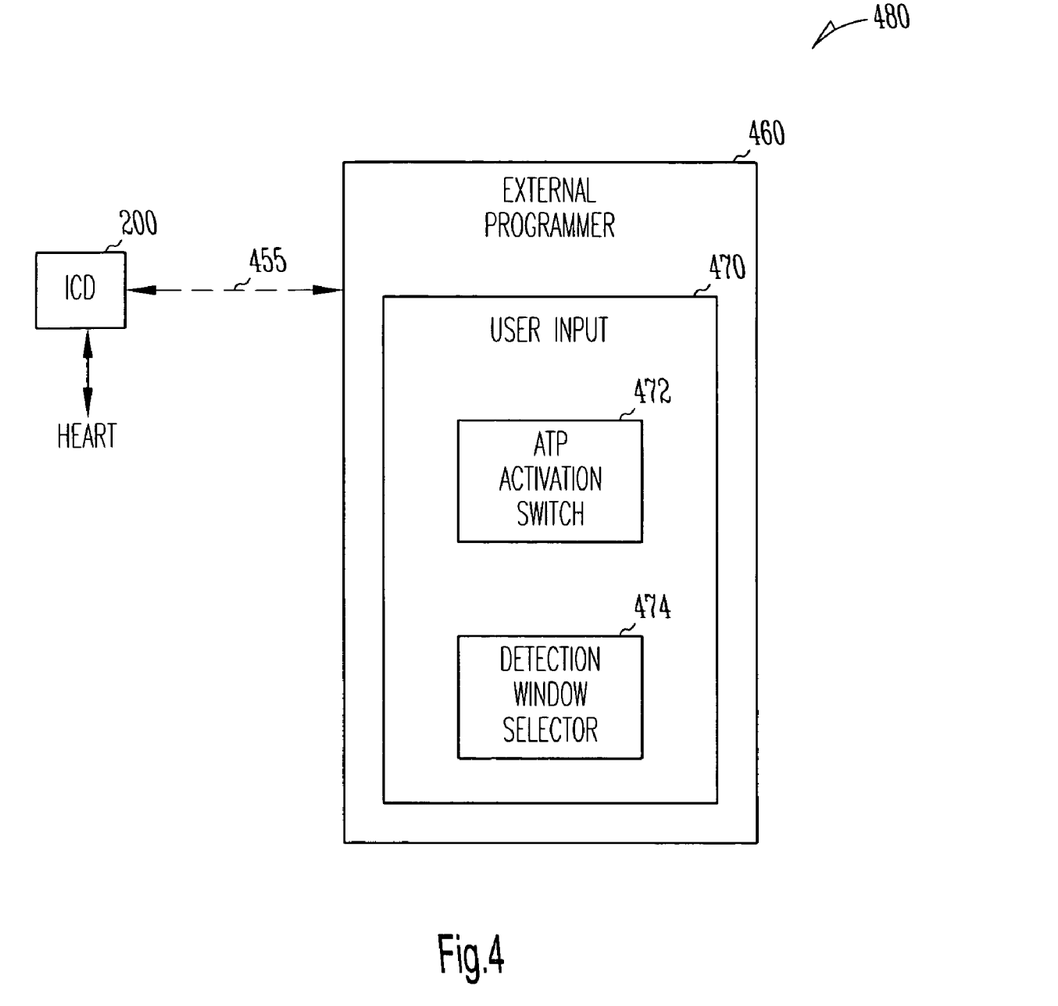
FIG. 4 is a block diagram showing one embodiment of portions a CRM system including the ICD and an external programmer.

FIG. 4 is a block diagram showing one embodiment of portions a CRM system 480 including ICD 200, an external programmer 460, and a telemetry link 455 providing for bidirectional communication between ICD 200 and external programmer 460. External programmer 460 includes a user input 470 as part of its user interface. User input 470 includes an ATP activation switch 472 to receive a user command for activating the ATP-BC mode operation. Upon receiving the user command, user input 470 produces the ATP activation command. The ATP activation command is transmitted to ICD 200 via telemetry link 455. In one embodiment, user input 470 includes an on/off (or yes/no) selector allowing an entry of the user command by an on-selection (or yes-selection). In one embodiment, user input 470 also includes a detection window selector 474 to receive selections relating detection windows each corresponding to at least one of the one or more predetermined threshold rates. In one embodiment, each detection window is defined by a heart rate window including two programmable threshold rates. In one embodiment, user input 470 includes an ATP-BC selector through which the user selects detection windows within which the ATP-BC mode is activated.

Figure 5:
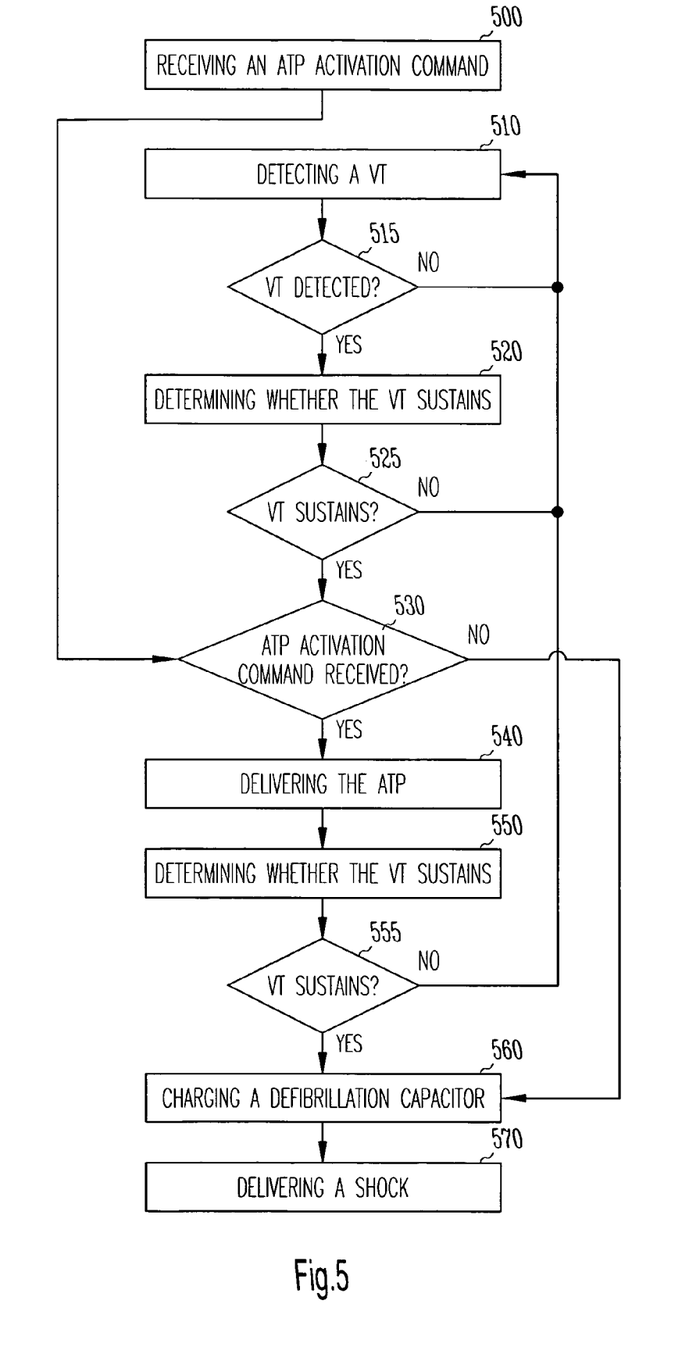
FIG. 5 is a flow chart illustrating an embodiment of a method for operating the ICD to deliver the ATP.

FIG. 5 is a flow chart illustrating an embodiment of a method for operating an ICD in the ATP-BC mode discussed above with reference to FIG. 1. The method allows for the ATP-BC mode operation to be activated only by a user. The user decides whether to activate the ATP-BC mode based on his/her understanding of how the mode operates and the cardiovascular conditions and other circumstances of the patient.

An ATP activation command is received at 500. The ATP-BC mode is activated by the ATP activation command until an ATP deactivation command is received.

The ICD detects a VT at 510. In one embodiment, the ICD continuously detects the VT regardless of whether the ATP-BC mode is active. If the VT is detected at 515, the ICD determines whether the VT sustains after being detected by performing the fast VT verification test at 520.

In one embodiment, if the VT sustains at 525 and the ATP activation command is received at 530, the ICD delivers the ATP at 540. In a specific embodiment, if the VT sustains at 525, the ATP activation command is received at 530, and the heart rate is below 250 bpm, the ICD delivers the ATP at 540. After the ATP is delivered, the ICD determines whether the VT sustains after the ATP delivery by performing the fast VT verification test at 550. If the VT sustains at 555, the ICD charges a defibrillation capacitor at 560, and delivers a shock at 570 after the charging is completed. In one embodiment, the ICD determines whether the VT sustains after the charging by performing the fast VT verification test, and delivers the shock of the VT sustains.

If the VT sustains at 525, but the ATP activation command is not received at 530, and/or the heart rate is 250 bpm or higher, the ICD charges one or more defibrillation capacitors at 560, and delivers a shock at 570 after the charging is completed. In one embodiment, the ICD determines whether the VT sustains after charging the one or more defibrillation capacitors by performing the fast VT verification test, and delivers the shock if the VT sustains.

It is to be understood that the above detailed description is intended to be illustrative, and not restrictive. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system comprising:
   a sensing circuit to sense a cardiac signal;
   a pacing circuit to deliver an anti-tachycardia pacing (ATP);
   a defibrillation circuit to deliver a shock, the defibrillation circuit including:
      a defibrillation capacitor to store an electrical energy for the shock; and
      a capacitor charging circuit to charge the defibrillation capacitor in response to a charging signal;
   a ventricular tachycardia (VT) detector to detect a VT based on at least the cardiac signal;
   a VT verification module programmed to receive a first VT verification command and a second VT verification command and perform a VT verification test to determine whether the VT sustains based on at least the cardiac signal after one of the first and second VT verification commands is received;
   a controller coupled to the pacing circuit, the defibrillation circuit, the VT detector, and the VT verification module, the controller programmed to receive an ATP activation command and an ATP deactivation command, activate an ATP before charge (ATP-BC) mode in response to the ATP activation command, and deactivate the ATP-BC mode in response to the ATP deactivation command, the controller including:
      an ATP activator to receive the ATP activation command and produce an ATP activation signal in response to a receipt of the ATP activation command;
      a first VT verification controller to issue the first VT verification command after the VT is detected and produce a first VT verification signal if the VT sustains after being detected;
      an ATP controller to detect a presence of the ATP activation signal and, if the ATP activation signal is present, to receive the first VT verification signal and control an ATP delivery after the first VT verification signal is received;
      a second VT verification controller to issue the second VT verification command after the ATP delivery and produce a second VT verification signal if the VT sustains after the ATP delivery;
      a charging controller to detect the presence of the ATP activation signal and, if the ATP activation signal is present, receive the second VT verification signal and produce the charging signal after the second VT verification signal is received, and if the ATP activation signal is not present, receive the first VT verification signal and produce the charging signal after the first VT verification signal is received; and
      a defibrillation controller to control a delivery of the shock after the charging of the defibrillation capacitor is completed; and
   a user input including an ATP activation switch to receive a user command and produce one of the ATP activation command and the ATP deactivation command based on the user command.

2. The system of claim 1, wherein the ATP activator includes a command input to receive the ATP activation command and a heart rate input to receive a heart rate, the ATP activator adapted to produce the ATP activation signal in response to the receipt of the ATP activation command if the heart rate is below a predetermined threshold rate.

3. The system of claim 1, wherein the VT verification module receives a third VT verification command and performs the VT verification test to determine whether the VT sustains after one of the first, second, and third VT verification commands is received, the controller further comprises a third VT verification controller to issue the third VT verification command while the defibrillation capacitor is being charged and produce a third VT verification signal if the VT sustains while the defibrillation capacitor is being charged.

4. The system of claim 3, wherein the VT verification module receives a fourth VT verification command and performs the VT verification test to determine whether the VT sustains after one of the first, second, third, and fourth VT verification commands are received, the controller further comprises a fourth VT verification controller to issue the fourth VT verification command after the charging of the defibrillation capacitor is completed and produce a fourth VT verification signal if the VT sustains after the charging of the defibrillation capacitor is completed, and the defibrillation controller receives the fourth VT verification signal and controls the delivery of the shock after the fourth VT verification signal is received.

5. The system of claim 1, wherein the VT detector comprises:
   a heart rate detector to detect a heart rate; and
   a comparator to compare the heart rate to one or more predetermined threshold rates.

6. The system of claim 1, wherein the VT detector comprises:
   a heart rate detector to detect a heart rate for each heart beat of a predetermined number of consecutive heart beats;
   a VT rate comparator to compare the heart rate for each heart beat to one or more predetermined VT threshold rates forming a detection window;
   a VT beat counter to count a number of fast beats each being a heart beat having a heart rate falling within the detection window; and
   a VT declaration module to declare that the VT is detected based on the number of fast beats and the predetermined number of consecutive heart beats.

7. The system of claim 6, wherein the VT declaration module comprises a VT detection comparator to compare the number of fast beats to a predetermined threshold number and declare that the VT is detected if the number of fast beats exceeds the predetermined threshold number.

8. The system of claim 6, wherein the VT declaration module comprises:
   a VT beat ratio calculator to calculate a VT beat ratio of the number of fast beats to the predetermined number of consecutive heart beats; and
   a VT detection comparator to compare the VT beat ratio to a predetermined threshold ratio and declare that the VT is detected if the VT beat ratio exceeds the predetermined threshold ratio.

9. The system of claim 1, wherein the VT verification module comprises:
   a heart rate detector to detect a heart rate for each heart beat of a predetermined number of consecutive heart beats;

a VT rate comparator to compare the heart rate for each heart beat to one or more predetermined VT threshold rates forming a detection window;

a VT beat counter to count a number of fast beats each being a heart beat having a heart rate falling within the detection window; and a VT declaration module to declare that the VT sustains based on the number of fast beats and the predetermined number of consecutive heart beats.

10. The system of claim 9, wherein the VT declaration module comprises a VT detection comparator to compare the number of fast beats to a predetermined threshold number and declare that the VT sustains if the number of fast beats exceeds the predetermined threshold number.

11. The system of claim 9, wherein the VT declaration module comprises
a VT beat ratio calculator to calculate a VT beat ratio of the number of fast beats to the predetermined number of consecutive heart beats; and
a VT detection comparator to compare the VT beat ratio to a predetermined threshold ratio and declare that the VT sustains if the VT beat ratio exceeds the predetermined threshold ratio.

12. The system of claim 1, wherein the controller further comprises a precharging controller to produce the charging signal after the VT is detected and before the ATP delivery.

13. The system of claim 1, further comprising an implantable metal can housing the sensing circuit, the pacing circuit, the defibrillation circuit, the VT detector, the VT verification module, and the controller.

14. The system of claim 13, further comprising an external programmer including the user input.

15. The system of claim 14, wherein the user input further comprises a detection window selector to receive selections relating detection windows each corresponding to at least one of the one or more predetermined threshold rates.

16. A method for operating an implantable cardioverter/defibrillator (ICD), comprising:
receiving a user command;
producing an anti-tachycardia pacing (ATP) activation command or an ATP deactivation command in response to the user command, the ATP activation command activating a feature including delivering an ATP; the ATP deactivation command deactivating the feature;
detecting a ventricular tachycardia (VT);
determining whether the VT sustains after being detected;
delivering the ATP if the ATP activation command is received and the VT sustains after being detected;
charging a capacitor if the ATP activation command is not received and the VT sustains after being detected;
determining whether the VT sustains after the delivering the ATP;
charging the capacitor if the VT sustains after the ATP is delivered; and
delivering a defibrillation shock after the capacitor is charged.

17. The method of claim 16, further including detecting a heart rate, and wherein delivering the ATP comprises delivering the ATP if the ATP activation command is received, the VT sustains after being detected, and the heart rate is below a predetermined threshold rate.

18. The method of claim 17, wherein delivering the ATP comprises delivering the ATP if the ATP activation command is received, the VT sustains after being detected, and the heart rate is below about 250 beats per minute.

19. The method of claim 16, further comprising detecting a ventricular fibrillation (VF).

20. The method of claim 16, wherein detecting the VT comprises:
detecting a heart rate for each heart beat of a predetermined number of consecutive heart beats;
comparing the heart rate for each of the consecutive heart beats to one or more threshold rates forming a detection window; and
declaring that the VT is detected if the heart rate falls within the detection window for at least a predetermined number of fast beats.

21. The method of claim 20, wherein detecting the VT comprises:
detecting a predetermined number of consecutive fast heart beats each having a heart rate falling within the detection window;
detecting the heart rate for each heart beat of the predetermined number of consecutive heart beats after the predetermined number of consecutive fast heart beats are detected;
comparing the heart rate for each of the consecutive heart beats to one or more threshold rates forming the detection window; and
declaring that the VT is detected if the heart rate falls within the detection window for at least the predetermined number of fast beats.

22. The method of claim 20, wherein detecting the VT comprises:
detecting the heart rate for each heart beat of about 10 consecutive heart beats;
comparing the heart rate for each of the about 10 consecutive heart beats to the one or more threshold rates forming the detection window; and
declaring that the VT is detected if the heart rate falls within the detection window for at least about 8 out of the about 10 consecutive heart beats.

23. The method of claim 22, wherein detecting the VT comprises:
detecting 3 consecutive fast beats each having a heart rate falls within the detection window;
detecting the heart rate for each heart beat of the about 10 consecutive heart beats after the 3 consecutive fast beats are detected;
comparing the heart rate for each of the about 10 consecutive heart beats to the one or more threshold rates forming the detection window; and
declaring that the VT is detected if the heart rate falls within the detection window for at least about 8 out of the about 10 consecutive heart beats.

24. The method of claim 20, wherein declaring that the VT is detected comprises declaring that the VT is detected if the heart rate falls within the detection window for at least a predetermined fraction of the predetermined number of consecutive heart beats.

25. The method of claim 20, wherein the one or more threshold rates comprises a lower threshold rate, and further comprising programming the lower threshold rate to about 180 beats per minute.

26. The method of claim 25, wherein the one or more threshold rates comprises an upper threshold rate, and further comprising programming the upper threshold rate to about 250 beats per minute.

27. The method of claim 16, wherein the determining whether the VT sustains after being detected and determining whether the VT sustains after the delivering the ATP each comprise performing a fast VT verification test.

28. The method of claim 27, wherein performing the fast VT verification test comprises:

detecting a heart rate for each of a predetermined number of consecutive heart beats;

comparing the heart rate for each of the consecutive heart beats to one or more predetermined threshold rates forming a detection window; and declaring that the VT sustains if the heart rate falls within the detection window for at least a predetermined number of fast beats.

29. The method of claim 28, further comprising determining whether the episode of VT sustains while the capacitor is being charged, and stopping charging the capacitor if the VT does not sustain.

30. The method of claim 29, further comprising determining whether the episode of VT sustains after the capacitor is charged, and wherein delivering the shock after the capacitor is charged comprises delivering the shock if the VT sustains after the capacitor is charged.

31. The method of claim 29, wherein the determining whether the VT sustains after being detected, determining whether the VT sustains after the delivering the ATP, determining whether the episode of VT sustains while the capacitor is being charged and determining whether the episode of VT sustains after the capacitor is charged each comprise performing a fast VT verification test.

32. The method of claim 28, wherein performing the fast VT verification test comprises:

detecting the heart rate for each of about 10 consecutive heart beats;

comparing the heart rate each of the 10 consecutive heart beats to the one or more threshold rates forming the detection window; and declaring that the VT sustains if the heart rate falls within the detection window for at least about 6 out of the about 10 consecutive heart beats.

33. The method of claim 28, wherein declaring that the VT sustains comprises declaring that the VT sustains if the heart rate exceeds the first threshold rate for at least a predetermined fraction of the predetermined number of consecutive heart beats.

34. The method of claim 33, wherein declaring that the VT sustains comprises declaring that the VT sustains if the heart rate exceeds the first threshold rate for at least about two third of the predetermined number of consecutive heart beats.

35. The method of claim 28, wherein the one or more threshold rates comprises a lower threshold rate, and further comprising programming the lower threshold rate to about 180 beats per minute.

36. The method of claim 35, wherein the one or more threshold rates comprises an upper threshold rate, and further comprising programming the upper threshold rate to about 250 beats per minute.

37. The method of claim 16, further comprising charging the capacitor while determining whether the VT sustains after being detected.

38. The method of claim 16, wherein delivering the ATP comprises delivering a first burst of about 8 pacing pulses at a first pacing interval upon an expiration of a coupling interval starting from the last sensed depolarization.

39. The method of claim 38, further comprising programming the coupled interval to an interval within a range of about 120 ms to 750 ms.

40. The method of claim 38, further comprising programming the first pacing interval to an interval calculated as a predetermined percentage of the coupling interval or a minimum pacing interval, whichever is longer.

41. The method of claim 40, further comprising programming the first pacing interval to an interval calculated as about 88% of the coupling interval or about 200 milliseconds, whichever is longer.

42. The method of claim 40, wherein delivering the ATP further comprises delivering a second burst of about 8 pacing pulses.

43. A cardiac rhythm management system comprising:
a sensing circuit to sense a cardiac signal;
a pacing circuit to deliver an anti-tachycardia pacing (ATP);
a defibrillation circuit to deliver a shock, the defibrillation circuit including:
    a defibrillation capacitor to store an electrical energy for the shock; and
    a capacitor charging circuit to charge the defibrillation capacitor in response to a charging signal;
a ventricular tachycardia (VT) detector to detect a VT based on at least the cardiac signal, the VT detector including:
    a heart rate detector to detect a heart rate for each heart beat of a predetermined number of consecutive heart beats;
    a VT rate comparator to compare the heart rate for each heart beat to one or more predetermined VT threshold rates forming a detection window;
    a VT beat counter to count a number of fast beats each being a heart beat having a heart rate falling within the detection window; and
    a VT declaration module to declare that the VT is detected based on the number of fast beats and the predetermined number of consecutive heart beats, the VT declaration module including:
        a VT beat ratio calculator to calculate a VT beat ratio of the number of fast beats to the predetermined number of consecutive heart beats; and
        a VT detection comparator to compare the VT beat ratio to a predetermined threshold ratio and declare that the VT is detected if the VT beat ratio exceeds the predetermined threshold ratio;
a VT verification module programmed to receive a first VT verification command and a second VT verification command and perform a VT verification test to determine whether the VT sustains based on at least the cardiac signal after one of the first and second VT verification commands is received; and
a controller coupled to the pacing circuit, the defibrillation circuit, the VT detector, and the VT verification module, the controller including:
    an ATP activator to receive an ATP activation command and produce an ATP activation signal in response to a receipt of the ATP activation command;
    a first VT verification controller to issue the first VT verification command after the VT is detected and produce a first VT verification signal if the VT sustains after being detected;
    an ATP controller to detect a presence of the ATP activation signal and, if the ATP activation signal is present, to receive the first VT verification signal and control an ATP delivery after the first VT verification signal is received;
    a second VT verification controller to issue the second VT verification command after the ATP delivery and produce a second VT verification signal if the VT sustains after the ATP delivery;
    a charging controller to detect the presence of the ATP activation signal and, if the ATP activation signal is present, receive the second VT verification signal and produce the charging signal after the second VT verification signal is received, and if the ATP activation signal is not present, receive the first VT verification signal and produce the charging signal after the first VT verification signal is received; and a defibrillation controller to control a delivery of the shock after the charging of the defibrillation capacitor is completed.

44. A cardiac rhythm management system comprising:

a sensing circuit to sense a cardiac signal;

a pacing circuit to deliver an anti-tachycardia pacing (ATP);

a defibrillation circuit to deliver a shock, the defibrillation circuit including:
  a defibrillation capacitor to store an electrical energy for the shock; and
  a capacitor charging circuit to charge the defibrillation capacitor in response to a charging signal;

a ventricular tachycardia (VT) detector to detect a VT based on at least the cardiac signal;

a VT verification module programmed to receive a first VT verification command and a second VT verification command and perform a VT verification test to determine whether the VT sustains based on at least the cardiac signal after one of the first and second VT verification commands is received, the VT verification module including:
  a heart rate detector to detect a heart rate for each heart beat of a predetermined number of consecutive heart beats;
  a VT rate comparator to compare the heart rate for each heart beat to one or more predetermined VT threshold rates forming a detection window;
  a VT beat counter to count a number of fast beats each being a heart beat having a heart rate falling within the detection window; and
  a VT declaration module to declare that the VT sustains based on the number of fast beats and the predetermined number of consecutive heart beats, the VT declaration module including:
    a VT beat ratio calculator to calculate a VT beat ratio of the number of fast beats to the predetermined number of consecutive heart beats; and
    a VT detection comparator to compare the VT beat ratio to a predetermined threshold ratio and declare that the VT sustains if the VT beat ratio exceeds the predetermined threshold ratio; and a controller coupled to the pacing circuit, the defibrillation circuit, the VT detector, and the VT verification module, the controller including:

an ATP activator to receive an ATP activation command and produce an ATP activation signal in response to a receipt of the ATP activation command;
  a first VT verification controller to issue the first VT verification command after the VT is detected and produce a first VT verification signal if the VT sustains after being detected;
  an ATP controller to detect a presence of the ATP activation signal and, if the ATP activation signal is present, to receive the first VT verification signal and control an ATP delivery after the first VT verification signal is received;
  a second VT verification controller to issue the second VT verification command after the ATP delivery and produce a second VT verification signal if the VT sustains after the ATP delivery;
  a charging controller to detect the presence of the ATP activation signal and, if the ATP activation signal is present, receive the second VT verification signal and produce the charging signal after the second VT verification signal is received, and if the ATP activation signal is not present, receive the first VT verification signal and produce the charging signal after the first VT verification signal is received; and
  a defibrillation controller to control a delivery of the shock after the charging of the defibrillation capacitor is completed.

45. A method for operating an implantable cardioverter/defibrillator (ICD), comprising;

receiving an anti-tachycardia pacing (ATP) activation command activating a feature including delivering an ATP;

detecting a ventricular tachycardia (VT);

determining whether the VT sustains after being detected;

delivering the ATP if the ATP activation command is received and the VT sustains after being detected;

charging a capacitor if the ATP activation command is not received and the VT sustains after being detected;

determining whether the VT sustains after the delivering the ATP;

charging the capacitor if the VT sustains after the ATP is delivered; and delivering a defibrillation shock after the capacitor is charged, wherein delivering the ATP comprises delivering a first burst of about 8 pacing pulses at a first pacing interval upon an expiration of a coupling interval starting from the last sensed depolarization.

* * * * *

UNITED STATES PATENT AND TRADEMARK OFFICE
CERTIFICATE OF CORRECTION

| | | |
|---|---|---|
| PATENT NO. | : 7,277,750 B2 | Page 1 of 1 |
| APPLICATION NO. | : 10/817751 | |
| DATED | : October 2, 2007 | |
| INVENTOR(S) | : Perschbacher et al. | |

It is certified that error appears in the above-identified patent and that said Letters Patent is hereby corrected as shown below:

In column 11, line 31, in Claim 1, after "to" insert -- : --.

In column 13, line 16, in Claim 11, after "comprises" insert -- : --.

In column 15, line 27, in Claim 32, after "of" insert -- the --.

In column 18, line 29, in Claim 45, after "comprising" delete ";" and insert -- : --, therefor.

Signed and Sealed this

Twenty-sixth Day of February, 2008

JON W. DUDAS
*Director of the United States Patent and Trademark Office*